United States Patent
Griffin

(10) Patent No.: US 6,835,840 B2
(45) Date of Patent: Dec. 28, 2004

(54) PROCESS FOR THE PREPARATION DIARYL-4-AMINO-PIPERIDINYL COMPOUNDS

(75) Inventor: Andrew Griffin, St. Laurent (CA)

(73) Assignee: AstraZeneca AB, Sodertalje (SE)

( * ) Notice: Subject to any disclaimer, the term of this patent is extended or adjusted under 35 U.S.C. 154(b) by 5 days.

(21) Appl. No.: 10/433,719

(22) PCT Filed: Dec. 13, 2001

(86) PCT No.: PCT/SE01/02780

§ 371 (c)(1),
(2), (4) Date: Jun. 15, 2003

(87) PCT Pub. No.: WO02/48108

PCT Pub. Date: Jun. 20, 2002

(65) Prior Publication Data

US 2004/0068112 A1 Apr. 8, 2004

(30) Foreign Application Priority Data

Dec. 15, 2000 (SE) .................................. PCT/SE00/02560
May 18, 2001 (SE) ............................................... 0101764

(51) Int. Cl.[7] ...................... C07D 211/58; C07D 401/06
(52) U.S. Cl. ......................... 546/223; 546/224; 546/193
(58) Field of Search ................................ 546/223, 224, 546/193

(56) References Cited

U.S. PATENT DOCUMENTS 6,436,959 B1 * 8/2002 Carson et al. ............... 514/326
6,710,179 B2 * 3/2004 Pelcman et al. ............ 546/223

FOREIGN PATENT DOCUMENTS

| EP | 0257583 A1 | 3/1988 |
| FR | 2430M A | 3/1964 |
| FR | 1517671 A | 2/1968 |
| WO | 9933806 A1 | 7/1999 |

OTHER PUBLICATIONS

Christopher G. Frost et al, "Recent developments in aromatic heteroatom coupling reactions," J. Chem. Soc., Perkin Trans, vol. 1, 1998, p. 2615–2623,.

* cited by examiner

Primary Examiner—Celia Chang
(74) Attorney, Agent, or Firm—Jianzhong Shen

(57) ABSTRACT

The present invention discloses a now and improved process for the preparation 1-substituted di-aryl-4-amino-piperidinyl compounds by a one-pot double arylation followed by optional deprotection step(s).

11 Claims, No Drawings

PROCESS FOR THE PREPARATION DIARYL-4-AMINO-PIPERIDINYL COMPOUNDS

This application is 371 of PCT/SE01/02780 filed Dec. 13, 2001.

FIELD OF THE INVENTION

The present invention is directed to a new process for the preparation of 1-substituted diaryl-4-amino-piperidinyl compounds. In further aspects, the present invention also relates to new intermediates used in said process.

BACKGROUND AND PRIOR ART

WO 98/28270 discloses a group of compounds, and processes for their preparation, to which 1-substituted diaryl-4-amino-piperidinyl compounds belongs.

WO 99/33806 discloses 4[aryl(piperidin-4-yl)] aminobenzamide compounds and processes for their preparation. The core of the process disclosed in WO99/33806 consists of a reductive amination followed by a second step wherein the previously prepared N-aryl-piperidineamine is reacted with a bromo, iodo or trifluoromethanesulfonyloxy substituted benzamide in the presence of a palladium catalyst a phosphine ligand and a base to give said (N-aryl, N-piperid-4-yl)aminobenzamide.

The first reaction step (reductive amination) is performed using an appropriate solvent/reducing agent combination such as 1,2-chloroethane or acetonitrile/NaBH(OAc)$_3$+acid catalyst; methanol/NaBH$_3$CN+acid catalyst; titanium isopropoxide/NaBH$_3$CN; methanol, ethanol or isopropanol/NaBH$_4$; alcoholic solvent/H$_2$+noble metal catalyst or 1,2-dichloroethane or acetonitrile/NaBH(OAc)$_3$+acid catalyst. The product of the first step is thereafter isolated and purified before the second step is performed. The second step is thereafter performed in a different solvent.

Thomas et al. in J. Med. Chem. discloses 4-[aryl (piperidin-4-yl)]aminobenzamide of similar structure as WO 99/33806. The compounds are prepared by a reductive amination step followed by a nucleophilic aromatic substitution step.

The process of the present invention provides 1-substituted diaryl-4-amino-piperidinyl compounds in an improved and simplified manufacturing process that, e.g. uses only commercially available starting materials and reagents, has less reaction and purification steps, gives easier purification of the final and intermediate compounds, uses only one solvent system throughout the whole process.

Thus, the object of the present invention is to provide a novel process suitable for use in large-scale synthesis. A further object of the present invention is to provide a process containing as few reaction steps as possible.

OUTLINE OF THE INVENTION

The present invention provides a new process for preparation of 1-substituted diaryl-4-amino piperidinyl compounds, hereinafter referred to as compounds of the invention. The compounds of the invention are useful in therapy, and in particular for the treatment of pain.

The process for preparing of 1-substituted diaryl-amino-piperidinyl compounds is schematically shown in Scheme 1 below.

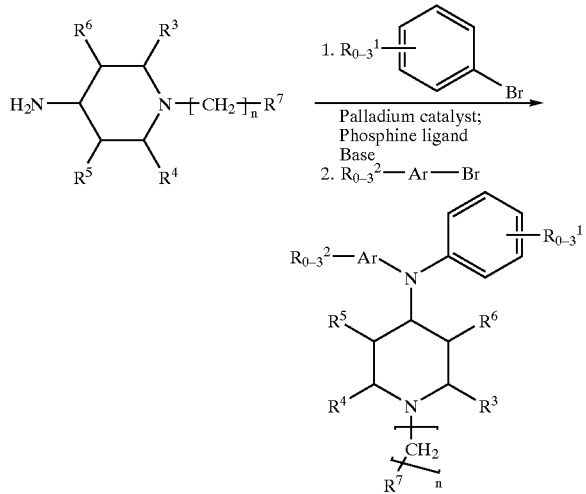

Scheme 1 wherein $R^1$ and $R^2$ are independently selected from the group consisting of hydrogen, hydroxy, halogen, $C_1$–$C_6$ alkyl, $C_1$–$C_6$ alkoxy, $C_1$–$C_6$ acyl, $C_1$–$C_6$ acyloxy, cyano, amino, nitro, $C_1$–$C_6$ acylamino, $C_1$–$C_6$ alkylamino, ($C_1$–$C_6$ alkyl)$_2$ amino, $C_1$–$C_6$ alkylthio, $C_1$–$C_6$ alkylsulfonyl, halogenated $C_1$–$C_6$ alkyl, halogenated $C_1$–$C_6$ alkoxy, CO—NR$^8$R$^9$ and $C_1$–$C_6$ alkoxycarbonyl;

$R^3$, $R^4$, $R^5$ and $R^6$ are independently selected from hydrogen and $C_1$–$C_6$ alkyl;

$R^7$ is selected from the group consisting of imidazolyl, thienyl, furanyl, pyrrolyl, thiazolyl, oxazolyl, pyridinyl, pyrazinyl, pyrimidinyl and phenyl, all optionally and independently mono-, di-, or tri-substituted with a R' group;

$R^8$ and $R^9$ are independently selected from hydrogen, $C_1$–$C_6$ alkyl, halogenated $C_1$–$C_6$ alkyl, phenyl, benzyl, all optionally and independently mono-, di-, or tri-substituted with a R" group;

Ar— is phenyl, 1-naphthyl or 2-naphthyl, each optionally substituted with 0 to 3 $R^2$ groups;

R' is independently selected from the group consisting of hydroxy, halogen, $C_1$–$C_6$ alkyl, $C_1$–$C_6$ alkoxy, $C_1$–$C_6$ acyl, $C_1$–$C_6$ acyloxy, cyano, amino, nitro, $C_1$–$C_6$ acylamino, $C_1$–$C_6$ alkylamino, ($C_1$–$C_6$ alkyl)$_2$amino, $C_1$–$C_6$ alkylthio, $C_1$–$C_6$ alkylsulfonyl, halogenated $C_1$–$C_6$ alkyl, halogenated $C_1$–$C_6$ alkoxy;

R" is independently selected from the group consisting of hydroxy, halogen, $C_1$–$C_6$ alkyl $C_1$–$C_6$ alkoxy, cyano, amino, nitro, $C_1$–$C_6$ alkylthio, halogenated $C_1$–$C_6$ alkyl, halogenated $C_1$–$C_6$ alkoxy; and n is 1, 2, 3, 4, 5, or 6.

A preferred embodiment of the present invention is the process according to Scheme 1, wherein $R^1$ and $R^2$ are independently selected from hydrogen, $C_1$–$C_6$ alkyl, $C_1$–$C_6$ alkoxy, hydroxy, halogen, cyano, amino, CO—NR$^8$R$^9$ and $C_1$–$C_6$ alkoxycarbonyl;

$R^3$, $R^4$, $R^5$ and $R^6$ are independently selected from hydrogen and $C_1$–$C_4$ alkyl;

$R^7$ is selected from the group consisting of imidazolyl, thienyl, furanyl, pyridinyl, and phenyl;

$R^8$ and $R^9$ are independently selected from hydrogen, $C_1$–$C_6$ alkyl, phenyl or benzyl; and n is an integer from 1 to 6.

A more preferred embodiment of the present invention is the process according to Scheme 1, wherein $R^1$ and $R^2$ are independently selected from hydrogen, $C_1$–$C_6$ alkyl, $C_1$–$C_6$ alkoxy, hydroxy, halogen, cyano, amino, CO—$NR^8R$ and $C_1$–$C_6$ alkoxycarbonyl;

$R^3$, $R^4$, $R^5$ and $R^6$ are hydrogen;

$R^7$ is selected from the group consisting of imidazolyl, furanyl, pyridinyl, and phenyl;

$R^8$ and $R^9$ are independently selected from hydrogen, ethyl and isopropyl, and n is 1.

An even more preferred embodiment of the present invention is the process according to Scheme 1, wherein $R^1$ and $R^2$ are independently selected from hydrogen, hydroxy, halogen, cyano, amino, CO—$NR^8R^9$ and $C_1$–$C_6$ alkoxycarbonyl;

$R^3$, $R^4$, $R^5$ and $R^6$ are hydrogen;

$R^7$ is selected from the group consisting of imidazolyl, furanyl, pyridinyl, and phenyl;

$R^8$ and $R^9$ are independently selected from hydrogen, ethyl and isopropyl, and n is 1.

Most preferred embodiment of the present invention is the process according to Scheme 1, wherein $R^1$ and $R^2$ are independently selected from hydrogen, halogen, cyano CO—$NR^8R^9$ and $C_1$–$C_6$ alkoxycarbonyl;

$R^3$, $R^4$, $R^5$ and $R^6$ are hydrogen;

$R^7$ is selected from the group consisting of imidazolyl, pyridinyl, and furanyl;

$R^8$ and $R^9$ are independently selected from hydrogen, ethyl and isopropyl; and n is 1.

Thus the process of the present invention can be described as comprising a one-pot double arylation step. It will be apparent for the skilled person that an optional deprotection step might have to be introduced after the one-pot double arylation step, due to interference/reactivity of the substituents. Reference is made to "Protective Groups in Organic Synthesis", 2nd edition, T. W. Greene & P. G. M. Wutz, Wiley-Interscience (1991). Example of a substituent that might need to be protected is hydroxy. A hydroxy substituent preferably protected as its methyl ether. Such methyl ether would then have to be cleaved after the one-pot double arylation step. This could for example be done by treating the product of the one-pot double arylation step with $BBr_3$ under standard conditions, such as 2–5 molar equivalents of $BBr_3$ in dichloromethane at −78° C.

The One-Pot Double Arylation Step

A one-pot double arylation step is a reaction that is performed in one pot but consists of two separate and distinct reaction steps (arylation couplings) that are performed consecutively without the need for any purification of intermediate compounds, work-up procedure, or change of solvent. The two reagents are added separately and the addition of the reagents is so timed as to allow the first reaction step to be completed before the next reagent is added to start the second reaction step.

The one-pot double arylation step of the present invention is performed by reacting 4-amino-piperidine of Formula II

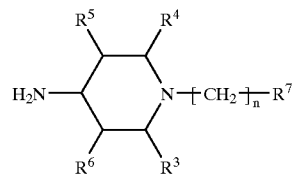

wherein $R^3$ to $R^7$, n, and R' are as described above in Scheme 1, with a first bromo compound of Formula III,

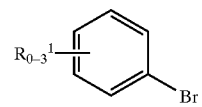

wherein $R^1$, $R^8$, $R^9$, and R" are as decribed above in Scheme 1, in the presence of a strong base, a palladium catalyst and a phosphine ligand. Upon completion of the first arylation step, a second bromo compound of Formula I

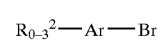

wherein $R^1$, $R^8$, $R^9$, R" and Ar are as decribed above in Scheme 1, and a strong base are added, without any isolation or purification of the reaction product of the first reaction step, to give the final product of Formula I in high yield.

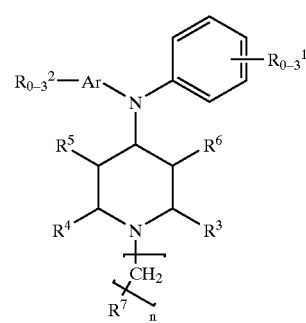

wherein $R^1$ to $R^9$, Ar, R', R" and n are as described above in Scheme 1. The final product might optionally have to been taken through a deprotection step.

Each reaction step of the one-pot double arylation in preferably done in an inert non-polar solvent system, such as toluene, at elevated temperature, such as around 80° C. or reflux, and for a few hours.

Palladium catalysts to be used in process of the present invention is chosen from a group consisting of $PdCl_2$, $Pd(OAc)_2$, $Pd(Ph_3P)_4(O)$ and tris(dibenzylideneacetone)-dipalladium(O), of which the last is preferred.

Phosphine ligands to be used in process of the present invention is chosen from a group of tri(o-tolyl phosphine), xantphos, 2-(di-t-butylphosphino)biphenyl and racemic BINAP, of which the latter is preferred.

Examples of strong bases that can be used in the process of the present invention comprise, but is not limited to, sodium tert. butoxide, cesium carbonate and sodium methoxide, of which sodium tert. butoxide is preferred.

The one-pot double arylation of the present invention is thus done without any isolation or purification of intermediate compounds. The one-pot double arylation of the present invention is further done in one solvent system for both arylation steps to Possible as well as preferred amounts and reaction conditions in the one-pot double arylation step are the following.

The molar equivalents relative to 4-aminopiperidine compound are for,

| | |
|---|---|
| 1$^{st}$ bromo compound | 0.9–1.2, preferably 0.95–1.1, |
| strong base, first addition | 1.05–1.5, preferably 1.1–1.4, |
| palladium catalyst and phosphine reagent | catalytic amount, preferably 0.01–0.2 |
| 2$^{nd}$ bromo compound | 1.0–2.0, preferable 1.3–1.7 |
| strong base, second addition | 1.0–2.0, preferable 1.3–1.7 |

It is also recommended to have the molar ratio between palladium catalyst and phosphine reagent as close to 1 as practically possible and the molar ratio between 2nd bromo compound and the second addition of base as close to 1 as practically possible.

The Deprotection Step

The optional deprotection can be accomplished by any known standard method to remove protecting groups that do not degrade the other parts of the molecule of the present invention. Reference is made to "Protective Groups in Organic Synthesis", 2nd edition, T. W. Greene & P. G. M. Wutz, Wiley-Interscience (1991).

The final product prepared according to the process of the present invention may thereafter be taken through further standard additional purification steps and/or converted into a suitable pharmaceutically acceptable salt.

It has also surprisingly been found that the two separate and distinct reaction steps (arylation couplings) can be performed in any order. This means that the process of the present invention can also be performed as is shown below in Scheme 2.

Scheme 2

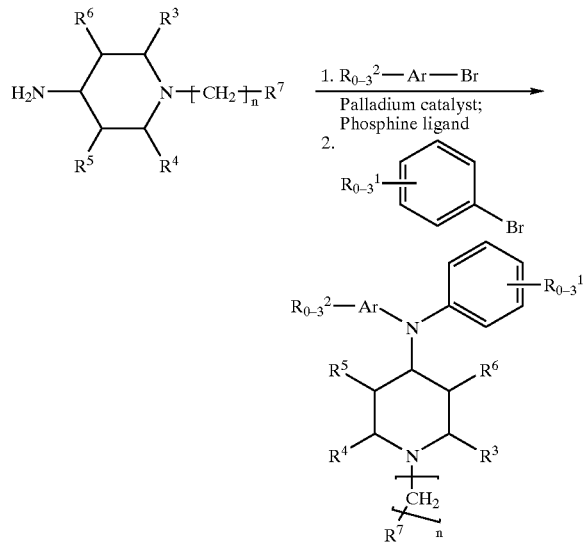

Intermediates

Another object of the present invention is to provide new intermediates that can be used in the preparation of compound of formula I.

Accordingly, a further aspect of the present invention is intermediate compound of Formula V and VI shown below,

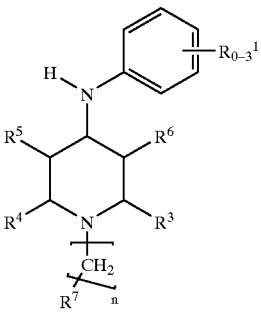

V

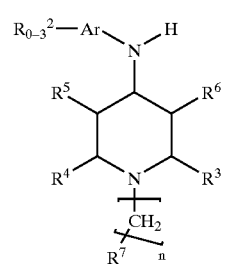

VI wherein $R^1$ to $R^9$, Ar, R', R" and n are as described in all the embodiments above.

The compounds prepared by the present invention can thereafter be converted into a pharmaceutically acceptable salt thereof, or optionally one of the substituents R or R can be converted into another functional group as described in Larock, Richard; Brown H. C.; Comprehensive Organic Transformations: A Guide to Functional Group Preparations, New York: VCH (1989), ISBN #-0471187186.

In one embodiment of the present invention $R^1$ is $C_1$–$C_6$ alkoxycarbonyl, e.g. tert. butyl ester, and $R^2$ to $R^9$, Ar, R', R" and n are as described in all the embodiments above. The $R^1 C_1$–$C_6$ alkoxycarbonyl group is eventually converted into a carboxamido group, e.g.

N,N-diethylcarboxamido, using standard procedure, e.g. by treating the ester with the corresponding amine in a suitable solvent.

In a preferred embodiment of the present invention R is N,N-diethylcarboxamido or N,N-diisopropylcarboxamido.

In a preferred embodiment of the present invention $R^2$ is independently selected from hydroxy, carboxamido, and halogen.

In a preferred embodiment of the present invention $R^3$, $R^4$, $R^5$, and $R^6$ are all hydrogen.

In a preferred embodiment of the present invention n is 1 and $R^7$ is a imidazolyl, furanyl, pyridinyl, or phenyl group.

DETAILED DESCRIPTION OF THE INVENTION

The present invention will now be described in more detail by the following examples, which should not be construed as limiting the invention. The process parameters given below can be adopted and adapted by the skilled person to suit his particular need.

EXAMPLES

Example 1

Preparation of N,N-diethyl-4-[[(3-methoxyphenyl)[1-(phenylmethyl)-4-piperidinyl]amino]benzamide To a solution of 500 μL of 3-bromoanisole (3.95 mmol) in 10 ml dry toluene was added 800 μl of 4-amino-N-benzyl piperidine (3.93 mmol), 197 mg racemic BINAP (0.32 mmol), 145 mg tris(dibenzylideneacetone)dipalladium(0) (0.16 mmol) and 530 mg sodium tert butoxide (5.52 mmol). The reaction was heated at 80° C. under a nitrogen atmosphere for 2 hours. The reaction was cooled to room temperature and 1.42 g of N,N-diethyl-4-bromobenzamide (5.55 mmol) and 530 mg of sodium tert butoxide (5.52 mmol) were added and the reaction heated to reflux. After 3 hours the solution was cooled to room temperature and the reaction diluted with ethyl acetate (50 ml) and water (30 ml) was added, filtered through celite and then the organic layer was separated, dried (MgSO$_4$), filtered and concentrated. The residue was purified by flash chromatography and then by a second flash chromatography to yield a pale orange oil. Finally, the oil was crystallized from hexanes containing a small amount of ethyl acetate and the solid collected by filtration to yield 1.163 g of a colourless solid (2.47 mmol; 63%).

1H NMR: (400 MHz, CDCl$_3$, TMS,): 7.31–7.23 (8H, m, Ar—H), 6.74–6.71 (1H, m, Ar), 6.66 (2H, d, J=9 Hz, Ar), 6.57–6.52 (2H, m, Ar), 3.87–3.80 (1H, m, CH), 3.77 (3H, s, OCH$_3$), 3.49 (2H, s, NCH$_2$Ar), 3.48 (41, br s, NCH$_2$), 2.96 (211, d, J=11.5 Hz, NCH$_2$), 2.11 (2H, t, J=12.5 Hz, NCH$_2$), 1.92 (2K, d, J=12.5 Hz, CH$_2$), 1.58–1.48 (2H, m, CH$_2$), 1.18 (6H, t, is J=6.5 Hz, CH$_3$)

Example 2

Preparation of N,N-diethyl-4[[(3-hydroxyphenyl)[1-(phenylmethyl)-4-piperdinyl]-amino]benzamide To a solution of N,N-diethyl-4-[[(3-methoxyphenyl)[1-(phenylmethyl)-4-piperidinyl]-amino]benzamide (1 eq) in CH$_2$Cl$_2$ at –78° C. was added 3 eq of BBr$_3$ (1 M in CH$_2$Cl$_2$). Stirred for approx. 45 minutes then at room temperature for 2 hours. MeOH was added followed by saturated NaHCO$_3$. The phases were separated and the aqueous layer extracted several times with CH$_2$Cl$_2$. The combined organic layers were dried over MgSO$_4$ and concentrated. Purification by flash chromatography over silica gel gave the title compound in 50–63% yield.

MS: (M+1) calculated: 458.62 (MH$^+$); (M+1) observed: 458.24 (MH$^+$). IR: Film HCl salt: 3047, 2974, 2531, 1600, 1471, 1455, 1283, 1186, 1093, 735, 701 cm$^{-1}$. 1H NMR: (400 MHz, CD$_3$OD) δ$_H$ 1.16 (br s, 6H, CH$_3$); 1.69–1.73 (m, 2H, CH$_2$); 2.22 (d, J=14 Hz, 211 CH$_2$); 3.27 (t, J=8 Hz, 2H, NCH$_2$); 3.35–3.51 (m, 6H, NCH$_2$) 4.27 (s, 2H, NCH$_2$Ar); 4.28–4.35 (m, 1H, NCHAr); 6.69 (d, J=9 Hz, 3H, Ar—H); 7.20–7.23 (m, 4H, Ar—H); 7.46 (s, 61, Ar—H).

Example 3

Preparation of N,N-diethyl-4-[[(3-cyanophenyl)[1-(phenylmethyl)-4-piperdinyl]amino]benzamide

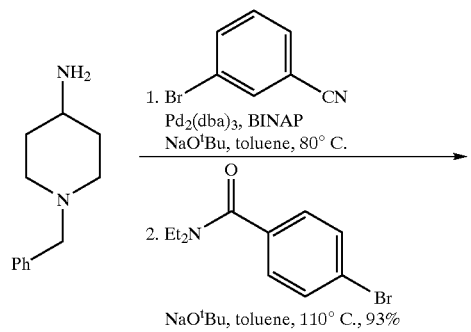

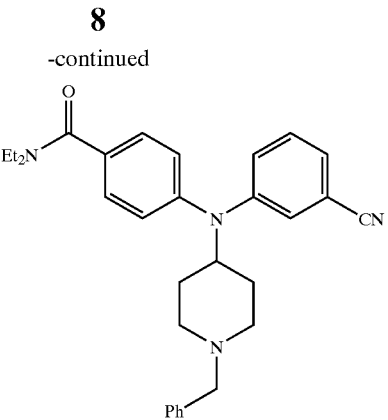

To a solution of 1.07 g of 3-bromobenzonitrile (5.88 mmol) in 15 ml dry toluene was added 1.2 mL of 4-amino-N-benzyl piperidine (5.89 mmol), 293 mg racemic BINAP (0.47 mmol), 215 mg tris(dibenzylideneacetone)dipalladium (0) (0.23 mmol) and 790 mg sodium tert butoxide (8.23 mmol). The reaction was heated at 80° C. under a nitrogen atmosphere for 4 hours. The reaction was cooled to room temperature and 2.26 g of N, N-diethyl-4-bromobenzamide (8.83 mmol) and 790 mg of sodium tert butoxide (8.23 mmol) were added and the reaction heated to reflux. After 20 hours the solution was cooled to room temperature and the reaction diluted with ethyl acetate (50 ml) and water (30 ml) was added, filtered through celite and then the organic layer was separated, dried (MgSO$_4$), filtered and concentrated. The residue was purified by flash chromatography, to yield an oil (2.54 g, 5.45 mmol; 93%).

(400 MHz, CDCl$_3$) δ$_H$ 1.36 (br s, 6H, CH$_3$); 1.441.54 (m, 2H, CH$_2$); 1.91 (d, J=12.5 Hz, 2H, CH$_2$); 2.12 (t J=12 Hz, 21, NCH$_2$); 2.97 (d, 3=12 Hz, 2H, NCH$_2$); 3.26–3.60 (m, 4H, NCH); 3.51 (s, 2H, NCH$_2$Ar); 3.79–3.86 (m, 1H, NCH); 6.86–6.89 (m, 1' Ar—H); 6.92–6.97 (m, 2H, Ar—H); 7.12–7.15 (m, 1H, Ar—H); 7.23–7.32 (m, 6H, Ar—H); 737–7.41 (m, 3H, Ar—H).

Example 4

Preparation of N,N-diisopropyl-4-[[(3-cyanophenyl)[1-(phenylmethyl)-4-piperidinyl]amino]benzamide

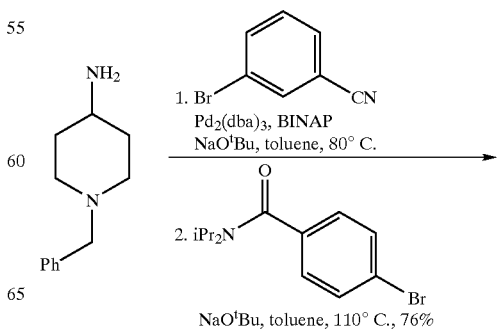

-continued

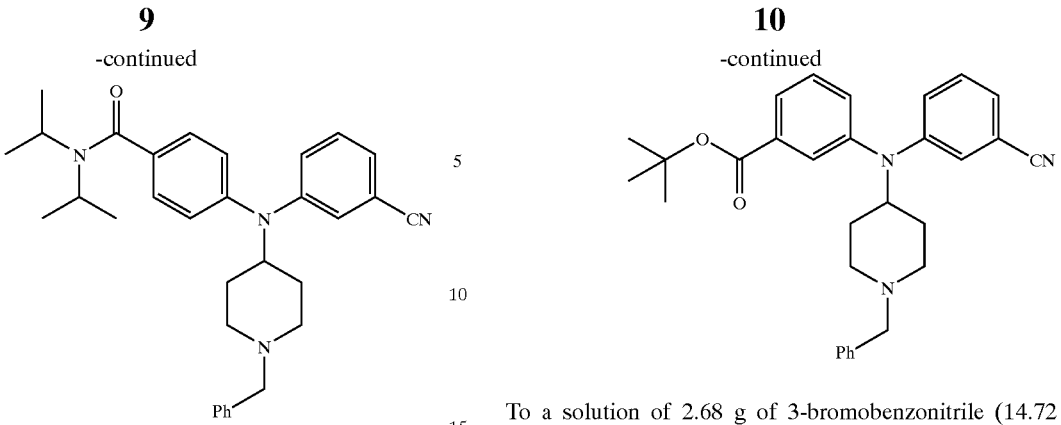

To a solution of 1.07 g of 3-bromobenzonitrile (5.88 mmol) in 15 ml dry toluene was added 1.2 mL of 4-amino-N-benzyl piperidine (5.89 mmol), 293 mg racemic BINAP (0.47 mmol), 215 mg tris(dibenzylideneacetone)dipalladium (0) (0.23 mmol) and 790 mg sodium tert butoxide (8.23 mmol). The reaction was heated at 80° C. under a nitrogen atmosphere for 4 hours. The reaction was cooled to room temperature and 2.34 g of N,N-diisopropyl-4-bromobenzamide (8.24 mmol) and 790 mg of sodium tert butoxide (8.23 mmol) were added and the reaction heated to reflux. After 20 hours the solution was cooled to room temperature and the reaction diluted with ethyl acetate (50 ml) and water (30 ml) was added, filtered through celite and then the organic layer was separated, dried ($MgSO_4$), filtered and concentrated. The residue was purified by flash chromatography to yield a foam (2.20 g, 4.45 mmol; 76%).

(400 MHz, $CDCl_3$) $\delta_H$, 1.37 (br s, 12H, $CH_3$); 1.45–1.55 (m, 2H, $CH_2$); 1.91 (d, J=13 Hz, 2H, $CH_2$); 2.12 (t, J=12 Hz, 2H, $NCH_2$); 2.97 (d, J=12 Hz, 2H, $NCH_2$); 3.51 (s, 2H, $NCH_2A$); 3.75 (br s, 2H, NCH); 3.77–3.84 (m, 1H, NCH); 6.82–6.84 (m, 1H, Ar—H); 6.93–6.96 (m, 3H, Ar—H); 7.109 (d, J=7.5 Hz, 1H, Ar—H); 7.22–7.36 (m, 8H, Ar—H).

Example 5

Preparation of-3-[[(3-cyanophenyl)[1-(phenylmethyl)-4-piperidinyl]amino]benzoic acid tert. butyl ester

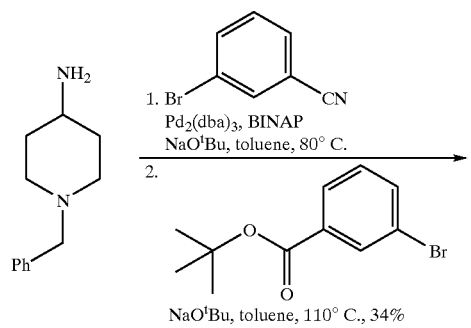

To a solution of 2.68 g of 3-bromobenzonitrile (14.72 mmol) in 40 ml dry toluene was added 3.0 mL of 4-amino-N-benzyl piperidine (14.73 mmol), 734 mg racemic BINAP (1.18 mmol), 540 mg tris(dibenzylideneacetone)dipalladium (O) (0.59 mmol) and 1.98 g sodium tert butoxide (20.63 mmol). The reaction was heated at 80° C. under a nitrogen atmosphere for 2 hours. The reaction was cooled to room temperature and 5.30 g of 3-bromobenzoic acid, tert butyl ester (20.62 mmol) and 1.98 mg of sodium tert butoxide (20.63 mmol) were added and the reaction heated to reflux. After 20 hours the solution was cooled to room temperature and the reaction diluted with ethyl acetate (100 ml) and water (50 ml) was added, filtered through celite and then the organic layer was separated, dried ($MgSO_4$), filtered and concentrated. The residue was purified by flash chromatography, eluting 30% ethyl acetate in hexanes to yield a yellow foam (2.36 g, 5.05 mmol; 34%).

(400 MHz, $CDCl_3$) $\delta_H$ 1.42–1.52 (m, 2H, $CH_2$); 1.60 (s, 9H, $^tBu$); 1.92 (d, J=12.5 Hz, 2H, $CH_2$); 2.09–2.15 (m, 2H, $NCH_2$); 2.97 (d, J=12 Hz, 2H, $NCH_2$); 3.50 (s, 2H, $NCH_2Ar$); 3.78–3.86 (m, 1H, NCH); 6.75–6.81 (m, 21H, Ar—H); 7.01–7.05 (m, 1H, Ar—H); 7.14–7.31 (m, 7H, Ar—H); 7.45 (t, J=8 Hz, 1H, Ar—H); 7.63–7.64 (m, 1H, Ar—H); 7.89–7.91 (m, 1H, Ar—H)

Intermediates (1-Benzyl-piperidin-4-yl)-(3-methoxy-phenyl)-amine prepared according to Example 1 above has the following physical data.

1H NMR: (400 MHz, $CDCl_3$, TMS,): 7.32–7.25 (5H, m, Ar), 7.05 (1H, t, J=8 Hz, Ar); 6.25–6.19 (2H, m, Ar), 6.14 (1H, s, Ar), 3.76 (3H, s, $OCH_3$), 3.52 (2H, s, $CH_2$), 3.31–3.22 (1H, m, CH), 2.85 (2H, d, J=11 Hz, $CH_2$), 2.14 (2H, t, J=11 Hz, $CH_2$), 2.03 (2H, d, J=11 Hz, $CH_2$), 1.47 (2H, q, J-11 Hz, $CH_2$)

What is claimed is:

1. A process for the preparation 1-substituted diaryl-4-amino-piperidinyl compound of Formula I

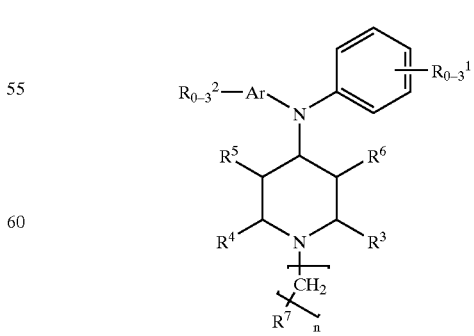

I wherein
R$^1$ and R$^2$ are independently selected from the group consisting of hydrogen, hydroxy, halogen, C$_1$–C$_6$ alkyl, C$_1$–C$_6$ alkoxy, C$_1$–C$_6$ acyl, C$_1$–C$_6$ acyloxy, cyano, amino, nitro, C$_1$–C$_6$ acylamino, C$_1$–C$_6$ alkylamino, (C$_1$–C$_6$ alkyl)$_2$amino, C$_1$–C$_6$ alkylthio, C$_1$–C$_6$ alkylsulfonyl, halogenated C$_1$–C$_6$ alkyl, halogenated C$_1$–C$_6$ alkoxy, CO—NR$^8$R$^9$ and C$_1$–C$_6$ alkoxycarbonyl;

R$^3$, R$^4$, R$^5$ and R$^6$ are independently selected from hydrogen and C$_1$–C$_6$ alkyl;

R$^7$ is selected from the group consisting of imidazolyl, thienyl, furanyl, pyrrolyl, thiazolyl, oxazolyl, pyridinyl, pyrazinyl, pyrimidinyl and phenyl, all optionally and independently mono-, di-, or tri-substituted with a R' group;

R$^8$ and R$^9$ are independently selected from hydrogen, C$_1$–C$_6$ alkyl, halogenated C$_1$–C$_6$ alkyl, phenyl, benzyl, all optionally and independently mono-, di-, or tri-substituted with a R" group;

Ar— is phenyl, 1-naphthyl or 2-naphthyl, each optionally substituted with 0 to 3 R$^2$ groups;

R' is independently selected from the group consisting of hydroxy, halogen, C$_1$–C$_6$ alkyl, C$_1$–C$_6$ alkoxy, C$_1$–C$_6$ acyl, C$_1$–C$_6$ acyloxy, cyano, amino, nitro, C$_1$–C$_6$ acylamino, C$_1$–C$_6$ alkyl)$_2$amino, (C$_1$–C$_6$ alkyl)$_2$amino, C$_1$–C$_6$ alkylthio, C$_1$–C$_6$ alkylsulfonyl, halogenated C$_1$–C$_6$ alkyl, halogenated C$_1$–C$_6$ alkoxy;

R" is independently selected from the group consisting of hydroxy, halogen, C$_1$–C$_6$ alkyl, C$_1$–C$_6$ alkoxy, cyano, amino, nitro, C$_1$–C$_6$ alkylthio, halogenated C$_1$–C$_6$ alkyl, halogenated C$_1$–C$_6$ alkoxy; and n is 1, 2, 3, 4, 5, or 6;

comprising the steps of;

A) a one-pot double arylation by a) reacting 4-amino piperidine of Formula II

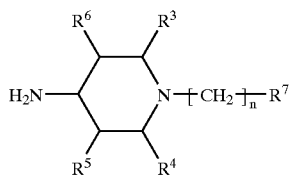

wherein R$^3$ to R$^7$ n, and R' are as described above, with a first bromo compound of Formula III,

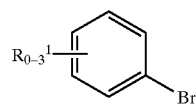

wherein R$^1$, R$^8$, R$^9$, and R" are as decribed above, in the presence of a strong base, a palladium catalyst and a phosphine ligand and b) thereafter reacting the product of reaction step a) with second bromo compound of Formula IV

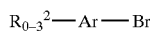

wherein R$^1$, R$^8$, R$^9$, R" and Ar are are as described above; and a strong base to give 1-substituted diaryl-4-amino-piperidinyl compounds of Formula I.

2. The process according to claim 1, characterized in that R$^1$ and R$^2$ are independently selected from hydrogen, C$_1$–C$_6$ alky, C$_1$–C$_6$ alkoxy, hydroxy, halogen, cyano, amino, CO—NR$^8$R$^9$ and C$_1$–C$_6$ alkoxycarbonyl;

R$^3$, R$^4$, R$^5$ and R are independently selected from hydrogen and C$_1$–C$_4$ alkyl;

R$^7$ is selected from the group consisting of imidazolyl, thienyl, furanyl, pyridinyl, and phenyl;

R$^8$ and R$^9$ are independently selected from hydrogen, C$_1$–C$_6$ alky, phenyl or bensyl; and n is an integer from 1 to 6.

3. The process according claim 1, characterized in that R$^1$ and R$^2$ are independently selected from hydrogen, C$_1$–C$_6$ alkyl, C$_1$–C$_6$ alkoxy, hydroxy, halogen, cyano, amino, CO—NR$_8$R$_9$ and C$_1$–C$_6$ alkoxycarbonyl;

R$_3$, R$_4$, R$_5$ and R$^6$ are hydrogen;

R$_7$ is selected from the group consisting of imidazolyl, thienyl, furanyl, pyridinyl, and phenyl;

R$_8$ and R$_9$ are independently selected from hydrogen, ethyl and isopropyl; and n is 1.

4. The process according to claim 1, characterized in that R$_1$ and R$_2$ are independently selected from hydrogen, hydroxy, halogen, cyano, amino, CO—NR$_8$R$_9$ and C$_1$–C$_6$ alkoxycarbonyl;

R$_3$, R$_4$, R$_5$ and R$^6$ are hydrogen;

R$_7$ is selected from the group consisting of imidazolyl, thienyl, furanyl, pyridinyl, and phenyl;

R$_8$ and R$_9$ are independently selected from hydrogen, ethyl and isopropyl; and n is 1.

5. The process according to claim 1, characterized in that R$_1$ and R$_2$ are independently selected from hydrogen, halogen, cyano, CO—NR$^8$R$^9$ and C$_1$–C$_6$ alkoxycarbonyl;

R$_3$, R$_4$, R$_5$ and R$^6$ are hydrogen;

R$_7$ is selected from the group consisting of imidazolyl, thienyl, furanyl, and pyridinyl;

R$_8$ and R$_9$ are independently selected from hydrogen, ethyl and isopropyl; and n is 1.

6. The process according to claim 1, characterized in that step b) is performed directly after reaction step a) without any isolation or purification of the product of reaction step a).

7. The process according to claim 1, characterized in that the palladium catalyst is PdCl$_2$, Pd(OAc)$_2$, Pd(Ph$_3$P)$_4$(O) or tris(dibenzylideneacetone)dipalladium(O).

8. The process according to claim 1, characterized in that phosphine ligand is tri(o-tolyl phosphine), xantphos, 2-(di-t-butylphosphino)biphenyl or racemic BINAP.

9. The process according to claim 1, characterized in that the both reaction steps a) and b) are performed in the same solvent system.

10. The process according to claim 5, characterized is that the solvent system is toluene.

11. The process according to claim 1, characterized in that the strong base is sodium tert. butoxide, cesium carbonate or sodium methoxide.

* * * * *

UNITED STATES PATENT AND TRADEMARK OFFICE
CERTIFICATE OF CORRECTION

PATENT NO. : 6,835,840 B2
DATED : December 28, 2004
INVENTOR(S) : Andrew Griffin It is certified that error appears in the above-identified patent and that said Letters Patent is hereby corrected as shown below:

Column 4,
Line 28, "decribed" is corrected to read -- described --;

Column 6,
Line 43, "R" is corrected to read -- $R^1$ --;

Column 12,
Lines 18, 30 and 40, "$R_3$, $R_4$, $R_5$" is corrected to read -- $R^3$, $R^4$, $R^5$ --;
Line 20, "$R_7$" is corrected to read -- $R^7$ --;
Lines 22 and 44, "$R_8$ and $R_9$" is corrected to read -- $R^8$ and $R^9$ --.

Signed and Sealed this

Twenty-ninth Day of March, 2005

JON W. DUDAS
*Director of the United States Patent and Trademark Office*